United States Patent [19]

Edwards

[11] Patent Number: 4,600,000
[45] Date of Patent: Jul. 15, 1986

[54] EXTERNAL FIXATION SYSTEM

[76] Inventor: Charles C. Edwards, 3907 Greenway, Baltimore, Md. 21218

[21] Appl. No.: 718,077

[22] Filed: Apr. 1, 1985

Related U.S. Application Data

[63] Continuation of Ser. No. 418,705, Sep. 16, 1982, abandoned.

[51] Int. Cl.$^4$ ............................................... A61F 5/04
[52] U.S. Cl. ..................... 128/92 A; 128/69; 128/83
[58] Field of Search ............... 128/92 A, 92 B, 92 C, 128/92 EB; 403/221, 222

[56] References Cited

U.S. PATENT DOCUMENTS

| | | | |
|---|---|---|---|
| 3,727,610 | 4/1973 | Riniker | 128/92 A |
| 4,006,740 | 2/1977 | Volkov et al. | 128/92 A |
| 4,502,473 | 3/1985 | Harris et al. | 128/92 A |

FOREIGN PATENT DOCUMENTS 974167  9/1950  France ................... 403/222

Primary Examiner—Richard J. Apley
Assistant Examiner—David J. Isabella
Attorney, Agent, or Firm—Connolly & Hutz

[57] ABSTRACT

An external fixation system includes as one of its frame components at least one dynamic coupling which is mounted to a respective frame rod. The coupling includes a sleeve member telescoped over the rod with a stop member on the rod on each side of the sleeve member. The stop member located toward the bone fracture may be adjustably locked to change its position on the rod and thus permit selective controlled sliding movement of the rod in the sleeve member.

15 Claims, 13 Drawing Figures

U.S. Patent   Jul. 15, 1986   Sheet 1 of 6   4,600,000
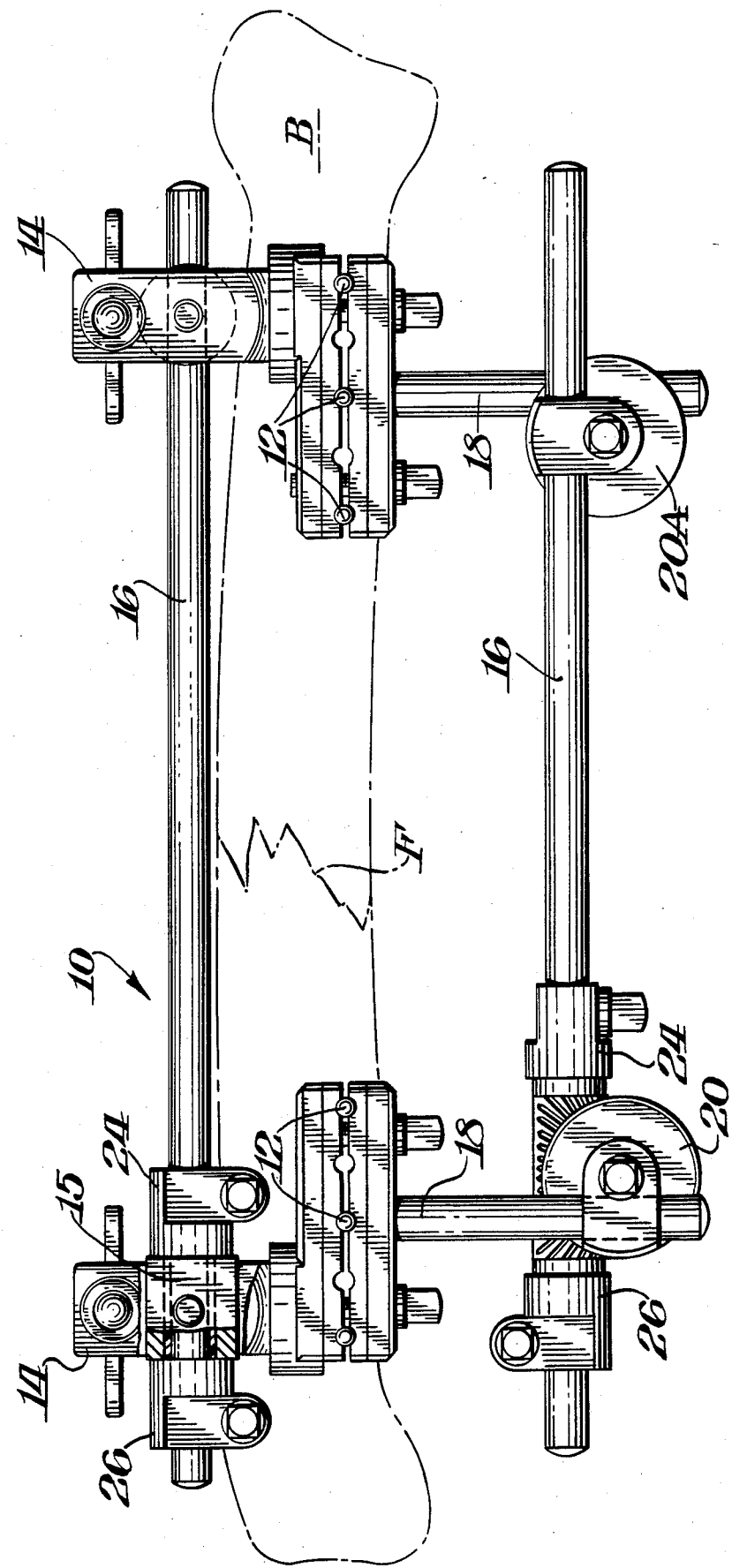

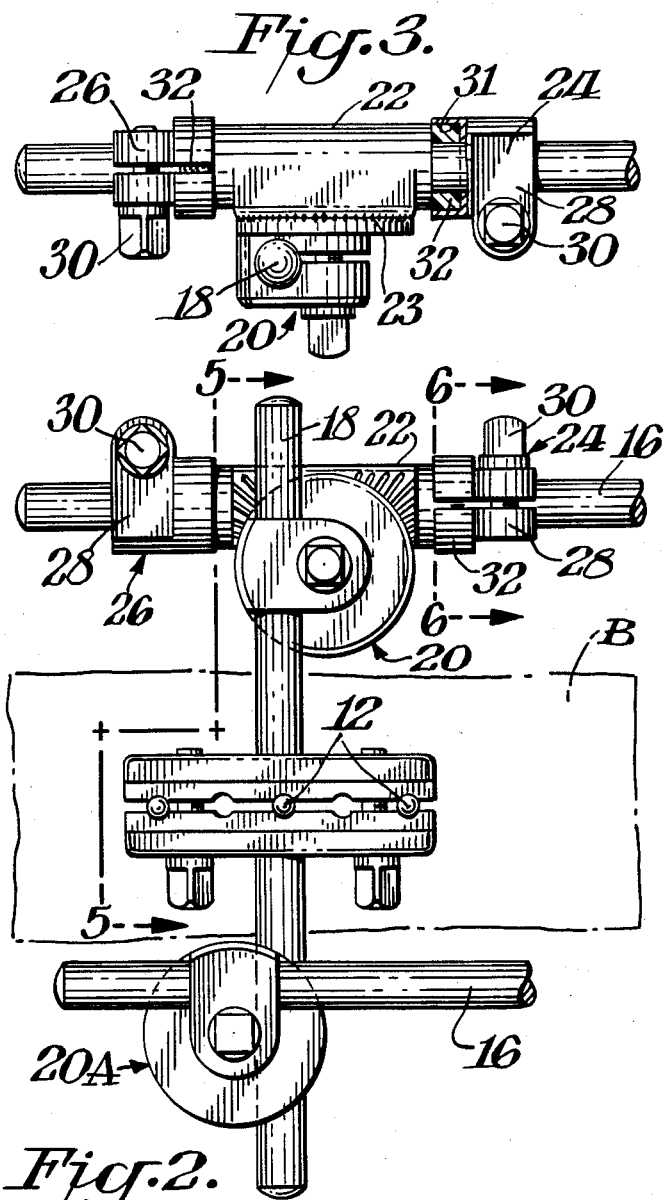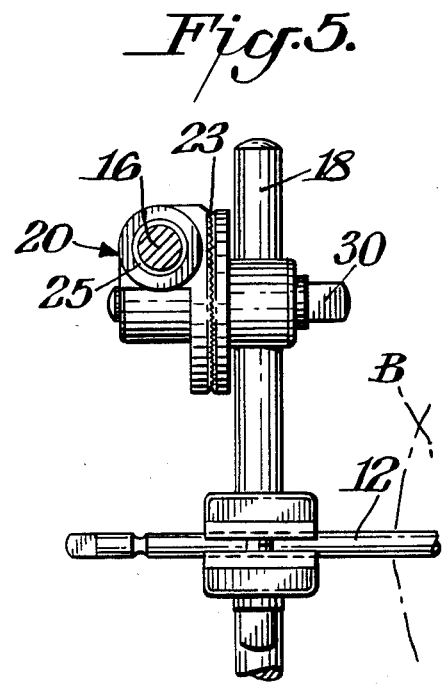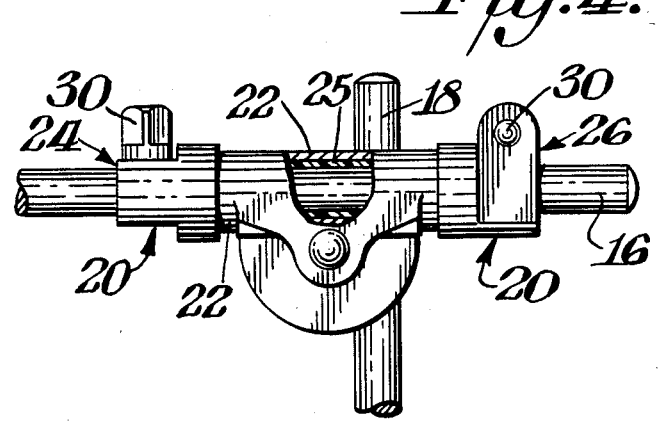

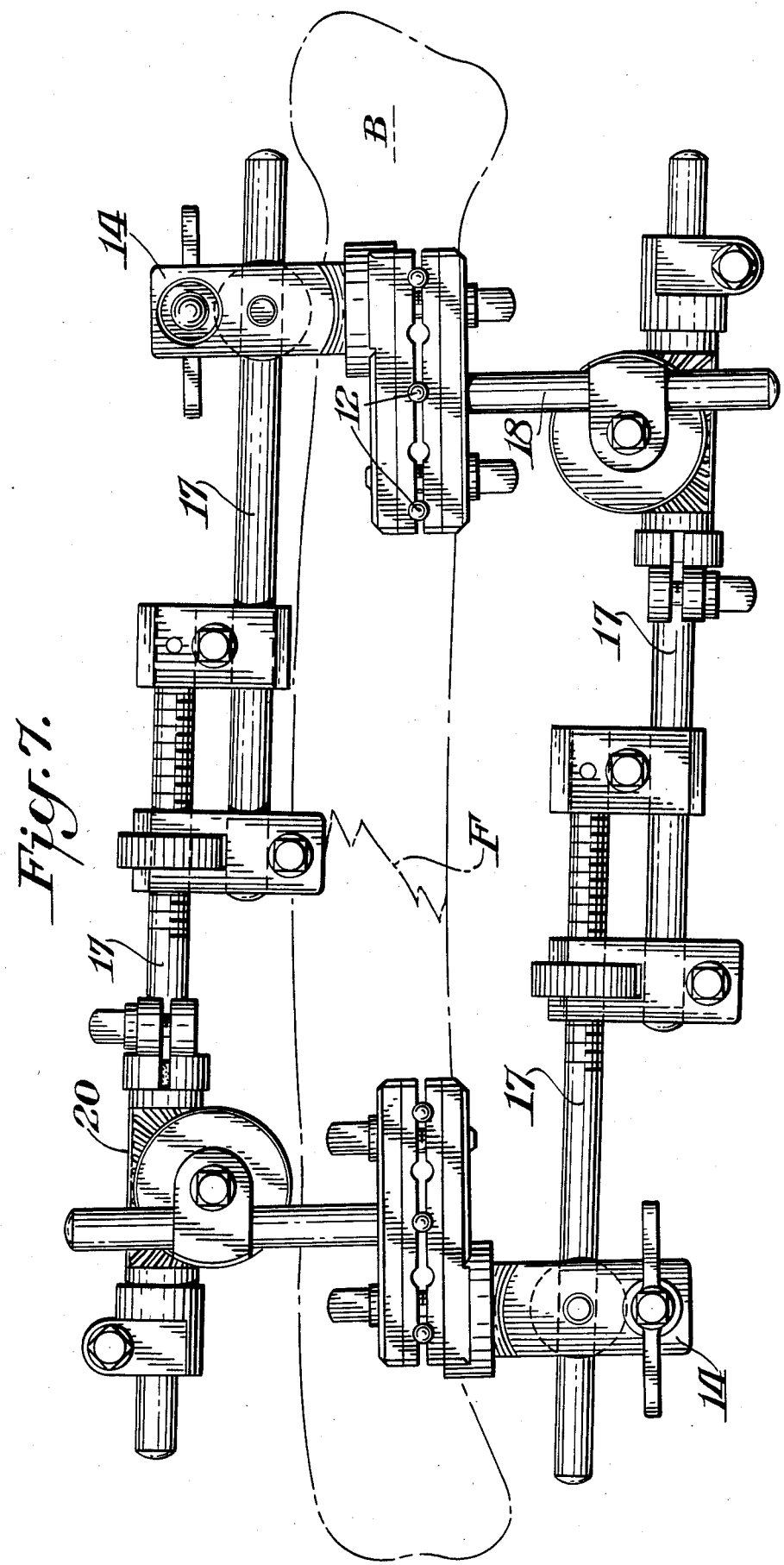

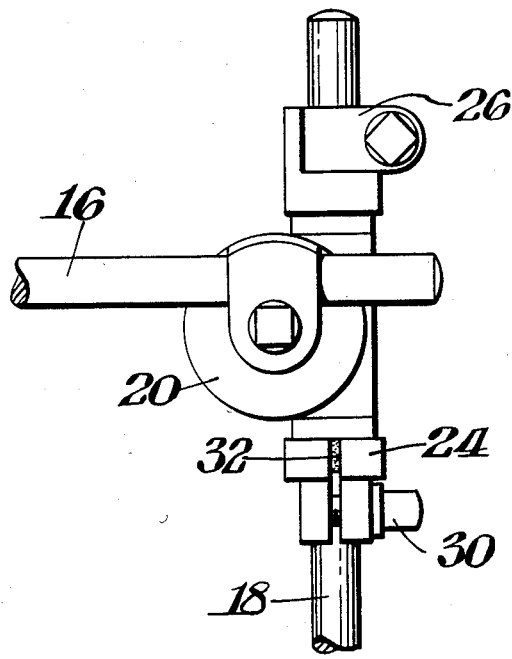
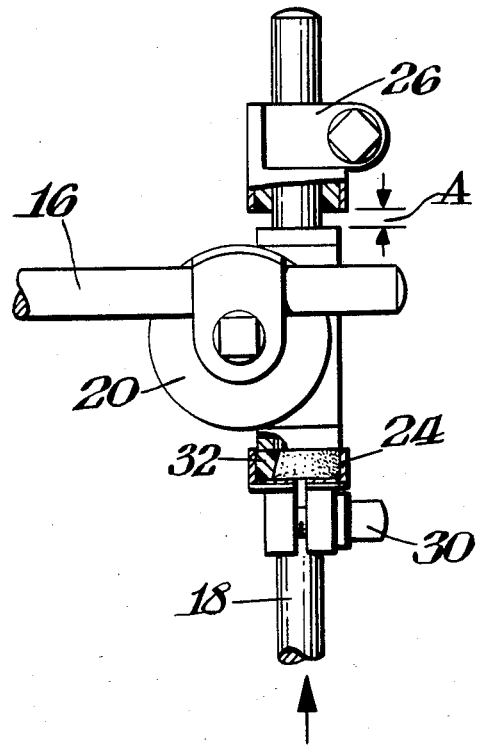
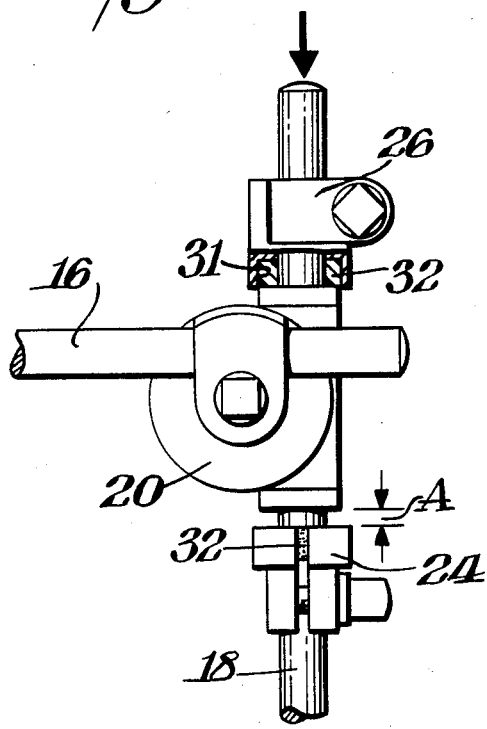

EXTERNAL FIXATION SYSTEM

CROSS-REFERENCE TO RELATED APPLICATION

This application is a continuation of application Ser. No. 418,705 filed Sept. 16, 1982, now abandoned.

BACKGROUND OF INVENTION

External fixation systems have been known for many decades. Such systems generally include a framework mounted around the bone fracture with a series of pins extending from the framework into the bone. Various forms of such systems are known including a quadrilateral system conventionally practiced with a Vidal frame as well as bilateral systems and unilateral systems. In general these systems promote bone union by stabilizing the position of the bone fragments. For some fracture patterns it is possible to compress the bone segments so as to achieve greater stability and speed union. However, in fractures with extensive comminution or bone loss, the fracture cannot be compressed without limit or shortening will occur.

In an exemplary practice, such frames are used for treating various leg bone fractures. When using rigid external fixation frames the majority of force from muscle pull or ambulation is transmitted through the frame and not the bone. After the healing process has begun, however, with the formation of soft callus between the bone ends, it would be desirable to permit the patient to exert a limited load on the bone and callus so as to encourage a stronger union. Conventional systems, however, either apply only static compression or static neutralization.

SUMMARY OF INVENTION

An object of this invention is to provide improvements in external fixation systems which permit the selective application of axial force across the fracture site while maintaining the desired level of baseline compression, if any.

A further object of this invention is to provide such a system which includes a dynamic coupling that can selectively maintain the frame in static neutralization or permit a relative sliding movement of a frame rod so that force could be applied across the fracture site while protecting the bone and fracture against excessive angulation or translation.

In accordance with this invention, an external fixation system includes as at least one of the frame components a dynamic coupling. The dynamic coupling comprises a sleeve member and a pair of stop members all of which would be mounted to a respective rod. The stop member which is located closer to the bone fracture could be adjustably positioned at various locations on its rod. When both stop members simultaneously abut the sleeve member, the frame is in static neutralization and will absorb any load applied thereto rather than permitting the load to bear directly against the bone fracture. When, however, the inner stop member is adjusted to a position out of contact with the sleeve member, a clearance is provided which would permit the rod to slide in the sleeve member a distance equal to the distance between the stop members. Under these conditions, a load would be applied directly to the bone fracture or healing callus.

The outer stop makes it possible to compress certain fractures with adjustable rods while allowing zero to unlimited impact load to cross the fracture site depending on the position of the inner stop.

One or both stop members may include cushioning means or shock absorbing members such as elastomeric washers disposed for contacting the sleeve member as the rod slides back and forth.

One or both stop members amy be in the form of a split sleeve mounted around the rod with adjustable clamp means spanning the open ends of the split sleeve so as to selectively permit the locked position of the stop member on the rod to be varied.

THE DRAWINGS

FIG. 1 is a side elevation view showing one form of an external fixation system which incorporates the invention;

FIG. 2 is a front elevation view partly in section of a portion of the system shown in FIG. 1;

FIG. 3 is a top plan view partly in section of the portion of the system shown in FIG. 2;

FIG. 4 is a rear elevation view partly in section of the portion of the system shown in FIGS. 2-3;

Figure 11:
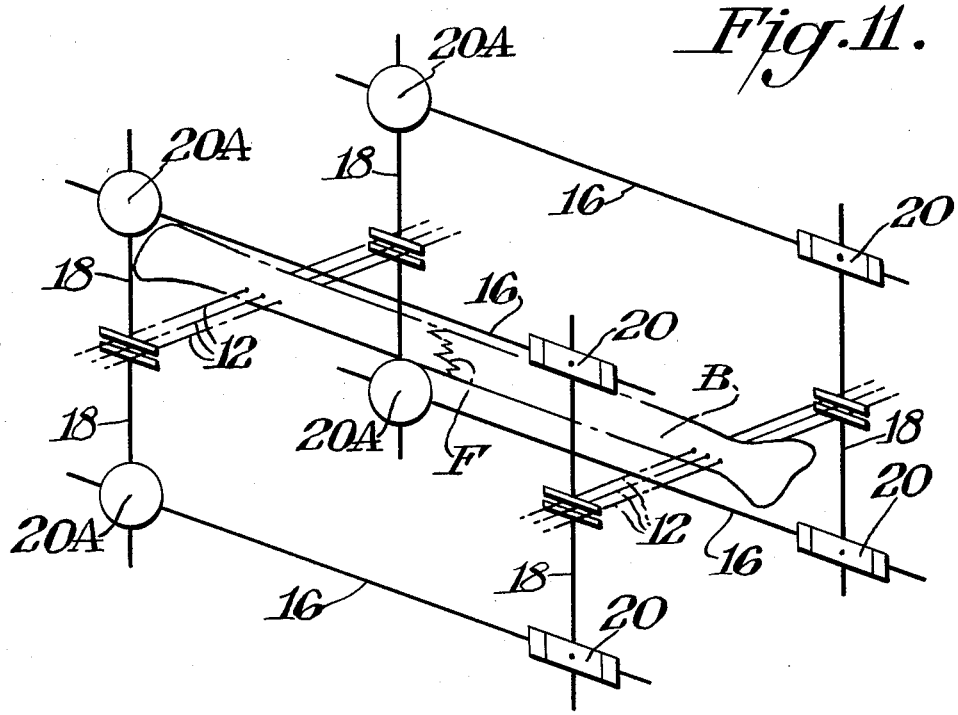
Figure 12:
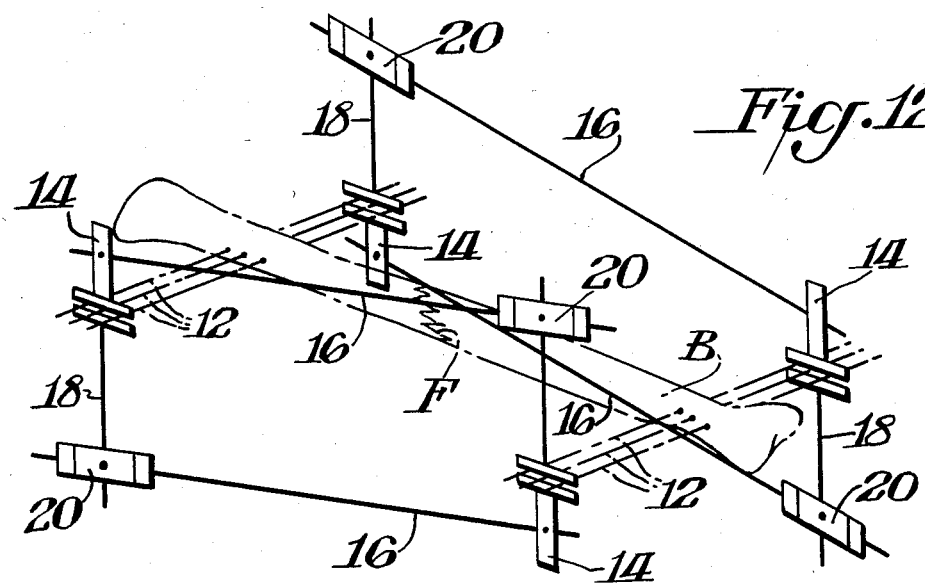
Figure 13:
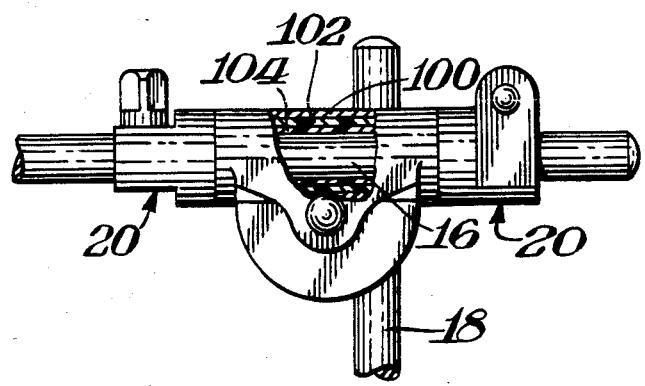

FIGS. 5 and 6 are cross-sectional views taken through FIG. 2 along the lines 5—5 and 6—6;

FIG. 7 is a side elevation view of an alternative external fixation system which also incorporates the invention;

FIGS. 8-10 are elevation views showing a portion of the system in different phases of operation; and FIGS. 11 12 are perspective views schematically illustrating the use of the invention in various frame arrangements; and FIG. 13 is a view similar to FIG. 4 showing a modified form of this invention.

DETAILED DESCRIPTION

In general the invention includes the incorporation of a novel dynamic coupling as at least one of the frame components in an external fixation system. In the late 1930's Dr. Raoul Hoffman designed an external fixation system. Such systems have been known in the art utilizing various frame forms. The invention will be described with particular reference to the Vidal frame which is a quadrilateral frame. It is to be understood, however, that such description is merely exemplary and that the invention may also be practiced with other forms of quadrilateral frames and indeed with other types of external fixation systems including bilateral and unilateral frames. Since the details of conventional external fixation systems are known, it is not necessary to repeat a description herein except as would facilitate an understanding of the invention. A description of an external fixation system of the type illustrated and the conventional components therein is found in a publication entitled "The Original Hoffman External Fixation System" copyright 1979 by Howmedica, Inc., the details of which are incorporated herein by reference thereto.

FIG. 1 illustrates an external fixation system 10 of the type conventionally known as a Vidal frame but which includes a number of dynamic couplings in accordance with this invention. As illustrated therein, system 10 is used for treating a fracture F. System 10 includes sets of transfixing pins 12 which are secured through the bone B on each side of fracture F. The transfixing pins 12 are then mounted to universal ball joints 14. In the known Vidal system, adjustable connecting rods would longitudinally span each pair of universal ball joints. In accordance with the practice of the invention, however, a more simplified form of rod 16 may be utilized. As illustrated in FIG. 1, rods 16 are simply straight members having the same diameter as the rods conventionally used in the known Vidal frame. Ball joints 14 also include outwardly extending rods 18 which are received in couplings.

In accordance with a further aspect of this invention the frame may be modified by having the dynamic couplings 20 on only one side of the bone. In this variation the ball joint, such as parts B-10 or B-11 of the aforenoted publication, would be modified by replacing the rod gripping portion with a novel housing insert 15 having a pair of nipples for fitting in the ball joint. The housing insert would have a bearing surface that would permit its rod to readily slide in accordance with the sliding permitted by couplings 20. The rod in the modified ball joint is preferably provided with stops, such as stops 26, at its outer ends.

Ordinarily with conventional Vidal frames, the couplings would be articulation couplings which would be locked to the longitudinal rods in such a manner that relative movement in the longitudinal direction between the rods and the couplings would be prevented. The conventional Vidal frame which includes adjustable connecting rods and conventional articulation couplings is capable of providing a compressive force to the bone or of maintaining the bone in a static neutralization condition. The rigid frame would absorb any load or weight that would have otherwise been transmitted to the bone.

While such conventional frame is suitable, particularly in the intial stages of healing, it is desirable in later stages of healing to permit the patient to apply some load to the bone so as to stimulate dynamic response in the bone since the bones are not static material but rather are viable and regenerate which makes the bones biodynamic. The invention replaces the conventional articulation couplings with dynamic couplings 20 constructed in such a manner as to function in either a static neutralization condition or dynamically by permitting the transmission of loads through the fracture site in addition to any desired level of baseline compression.

FIGS. 2-6 show the details of dynamic coupling 20. As indicated therein, coupling 20 essentially comprises a central sleeve member 22 with a stop member 24, 26 on each side thereof. FIG. 5 illustrates sleeve member 22 to include ratchet formations 23 for providing angular adjustment of rod 16. As illustrated in FIG. 5, sleeve member 22 includes structure to the right hand side of ratchet formation 23 for receiving depending rod 18. The structure to the right hand or inner side of ratchet formations 23 can be generally the same as corresponding structure in conventional articulation couplings. The structure to the outward side of ratchet formation 23, however, is novel and is so designed as to permit a dynamic coupling to result.

As a further aspect of the invention, the ratchet formations 23 could be replaced with homogeneously roughened facing surfaces prepared by casting or other suitable methods. This would permit a virtually infinite number of gradations in the relative angular position between rods 16 and 18, thereby making parallelity of the longitudinal rods 16 easier to achieve, thus reducing friction against axial sliding.

As illustrated in FIG. 4, sleeve member 22 includes a liner 25 made of a material such as Teflon to facilitate a sliding movement of rod 16 within sleeve member 22.

Stop member 26 is located toward the outer end of rod 16 and may be referred to as a remote stop member in that it would be remote from the fracture. Stop member 26 functions primarily to provide an outer limit for the relative path of travel of rod 16 through sleeve member 22. This makes it possible to apply compression across the fracture site either manually or with adjustable rods. Stop member 26 is illustrated in a form that permits its location on rod 16 to be varied. Once locked in place, however, it would remain stationary during the healing process. The adjustability feature of stop member 26 is also desirable for convenience of assembling the components of coupling 20. From a concept standpoint, however, stop member 26 need not be adjustably mounted and could take any suitable form such as being a cap friction fit over the end of rod 16. In the illustrated form, however, stop member 26 is a split sleeve having a pair of offset flanges 28 at the open ends thereof with a suitable fastener 30 such as a threaded fastener serving as a clamp to lock stop member 26 in place at a desired location on rod 16.

Stop member 24 is of similar construction to remote stop member 26. Stop member 24 may be considered as an inner stop member in that it is located closer to the bone fracture. Inner stop member 24 serves an important function in permitting and controlling the amount of back and forth movement of rod 16 in sleeve member 20. Accordingly, inner stop member 24 should be adjustably locked to rod 16 in such a manner that its position can be changed when desired.

Another desirable feature of this invention is the inclusion of cushioning members or shock absorbing means in each stop member located in the path of relative movement of the sleeve member 22 with respect to the moving rod 16. In the preferred form of this invention, the shock absorbing means is an elastomeric washer 32 which absorbs energy of impact upon axial loading and dampens the noise which would otherwise result upon contact of metal to metal when sleeve member 22 is contacted by each stop member. Any suitable cushioning or shock absorbing material would be used. The material, however, should be autoclavable high temperature and high performance material. A material commercially known under the 3M trademark FLUOREL may be satisfactorily used.

In the practice of the invention, if it is desired to initially apply a compressive force to the bone, a conventional external fixation system such as a Vidal frame could be used, with either standard or dynamic couplings 20. Alternatively at a suitable time during the healing process the articulation couplings would be sequentially replaced by the dynamic couplings 20 of this invention. Where, for example, a quadrilateral frame is used, the sequential replacements could be made without affecting the static condition of the bone. During this early stage of healing, the components of coupling 20 would be in the position indicated in FIG. 8 where each of the stop members 24 and 26 is juxtaposed sleeve member 22. While in this position the frame is in the static condition which would prevent a load being applied or transmitted through the fracture cite. When it is determined that partial physiological loading would be desired to stimulate healing, locking member 30 on inner adjustable stop 24 would be manipulated to loosen inner stop 24 and inner stop 24 would be moved away from sleeve member 22. During this initial stage for stimulating dynamic response, the distance "A" that stop member 24 would be moved might be about 1-2 mm. The gap "A" would thus permit relative sliding movement of rod 16 in sleeve member 22 by the distance of that gap. As the healing process continues and the deformable callus strengthens, it may be desirable to permit greater movement. In this case the position of stop member 24 would be adjusted to provide an even greater gap. As is apparent from FIGS. 9 and 10, stop members 24, 26 defined the ends of the path of movement. Thus, for example, coupling 20 at one extreme condition would have remote stop member 26 abutting against sleeve member 22. In the other extreme condition, stop member 24 would abut against sleeve member 22.

In order to alter the frame in such a way as to permit more fracture flexibility and facilitate the latter stages of fracture healing, the set screws 30 on either the standard or dynamic couplings can be loosened. As another aspect of this invention screws 30 are flanged or otherwise modified to prevent their dislodgement after loosening. Loosening the screws has two benefits in the latter stages of fracture healing: (1) to provide greater freedom of motion in all planes; and (2) to facilitate axial translation (fracture site loading) by reducing friction against sliding in cases where the longitudinal rods are not parallel.

A particular advantage of the dynamic couplings in accordance with this invention is that the very same elements may be used for both static neutralization and various gradations of a dynamic condition by merely making slight manipulations rather than requiring major manipulations or complete substitutions of components.

The dynamic coupling would include the conventional coupling components so that the coupling may also be selectively adjusted to vary the orientation of the rod 16 or 17 about its own axis and about an axis perpendicular to its own axis as well as linearly in a vertical plane which are the adjustments achievable with conventional articulation couplings.

In the illustrated system where the invention is used with fractures of large bones, a 8 mm rod 16 would be used for sliding in sleeve member 22 of generally the same diameter. Rod 16 would be available in several lengths in accordance with the desired application. To facilitate the sliding action where a plurality of rods 16 and dynamic couplings are used, it is desired to have the rods 16 as parallel as possible. However, the later described double bore design may be used in cases where the rods cannot be made relatively parallel. As previously indicated, each stop member preferably has a washer 32 affixed in a respective recess 31 of its stop member to eliminate clicking noise during fracture unloading during ambulation, to buffer against excessive compression across the fracture and fixateur and to absorb impact loads. The washer should have medium elasticity such as 50 durometers and might be several milimeters in thickness. Stop members 24, 26 as well as sleeve member 22 may be made from stainless steel with set screws 30 functioning to lock each stop member in place. Where, however, other size bones or different applications are being used, the dimensions of the components and their materials might differ in accordance with the desired results.

As previously indicated, the specific description herein of the dynamic couplings being incorporated in a specific form of Vidal frame is not intended to be limiting. FIGS. 11 and 12, for example, show other variations where the dynamic couplings 20 are located differently. These variations also include the conventional articulation couplings indicated by the reference numeral 20A where appropriate. It is also noted that the same reference numerals are used for the various universal ball joints and adjustable connecting rods although various frame arrangements may require the utilization of different variations of those components.

As also previously noted, the invention is not limited to the practice of a Vidal frame. Rather the invention can be used with any form of external fixation system with appropriate modification.

The present invention which includes dynamic couplings thus allows the transmission of controlled axial loading to a fracture stabilized by an external fixation system while simultaneously maintaining a preset minimum compressive force if desired (see FIG. 7) and preventing significant angular or torsional displacements across the fracture. The invention provides a general method for applying increased axial load to a fracture by means of a dynamic coupling. In the preferred practice of the invention, a sliding rod/coupling articulation system is used. The invention may be practiced by interposing a deformable material between the rod and coupling and by providing a sliding joint within the coupling which is attached to a standard free rod or the rod portion of an adjustable rod. Advantageously the invention allows physiological axial loading of a healing fracture by use of components which are compatible with standard Hoffman external fixation system components.

As previously described, the invention encompasses various features to overcome the increased friction against sliding which results from minor non-parallelity of the longitudinal rods (e.g. 16 or 17). In certain complex cases, however, major divergence of the longitudinal rods cannot be avoided. In this circumstance a double bore dynamic coupling (DBDC) is used as a further aspect of this invention. The DBDC compensates for rod divergence by allowing an inner sleeve to tilt within an outer housing.

The DBDC consists of a housing 100, an inner sleeve 102 and a stabilizing insert 104 (FIG. 13).

The housing is split diametrically in order to place or remove the stabilizing insert which wedges between the housing and inner sleeve. The bore within the housing is reconstituted by assemblying the two pieces of the housing by means of interlocking edges on one side of the housing and the coupling set screw on the other.

One refinement of this aspect of the invention is the provision of a plurality of stabilizing inserts of varying thicknesses. By replacing thicker inserts with thinner inserts as healing progresses, greater freedom of motion and efficiency of sliding are promoted.

The dynamic coupling and the various other aspects of this invention should make it possible for the healing physician to better match the mechanical characteristics of the external fixation device with the biologic needs of the fracture.

What is claimed is:

1. In an external fixation system wherein sets of pins are mounted from a frame on longitudinally opposite sides of a bone fracture, the improvement being said frame including a coupling comprising a rod for being generally longitudinally disposed from one set of pins on one side of the fracture to another set of pins on the other side of the fracture, a sleeve member having a longitudinal passageway extending therethrough, said rod being slidably positioned in said sleeve member, remote stop means coupled to said rod on the side of said sleeve member remote from the fracture, inner stop means coupled to said rod on the side of said sleeve member toward the fracture, adjustable locking means for selectively locking said inner stop means to said rod at a preselected position thereon to control the distance between said stop means whereby the degree of sliding movement of said rod within said sleeve member may be varied to provide a dynamic coupling thereof, said remote stop means and said inner stop means being coupled to said rod without any other components between each stop means and said sleeve whereby said sleeve may directly contact said stop means during said sliding movement, said sleeve member comprising a housing having a longitudinal bore, an inner sleeve positioned in said longitudinal bore and slidably receiving said rod, the outer diameter of said inner sleeve being smaller than the inner diameter of said longitudinal bore to provide clearance between said inner sleeve and the inner surface of said bore whereby said sleeve may be tilted to a position within said bore which is nonparallel with respect to said bore, a stabilizing insert being removably positioned within said housing in said clearance to prevent tilting of said inner sleeve within said bore, and said housing being adapted to be disassembled to permit removal of said insert to permit tilting of said inner sleeve within said outer bore.

2. The system of claim 1 including shock absorber means in at least one of said stop means disposed toward said sleeve member.

3. The system of claim 2 including shock absorber means in each of said stop means.

4. The system of claim 2 wherein said shock absorber means is a washer mounted in its stop means around said rod.

5. The system of claim 4 wherein said washer is made from an elastomeric material.

6. The system of claim 1 wherein said inner stop means is a split sleeve mounted around said rod, and said adjustable locking means comprises clamp means spanning the open ends of said split sleeve.

7. The system of claim 6 wherein said shock absorbing means is a washer mounted in said split sleeve around said rod disposed toward said sleeve member.

8. The system of claim 7 wherein each of said stop means is a split sleeve having a washer therein.

9. The system of claim 1 wherein said coupling further includes means for selectively adjusting the orientation of said rod about its own axis and about an axis perpendicular to its own axis and linearly in a vertical plane.

10. The system of claim 1 including a plurality of said couplings.

11. The system of claim 10 wherein said frame is a quadrilateral frame, and said coupling being mounted at selected corners of said frame.

12. The system of claim 11 wherein at least one of said rods is a single straight element spanning a respective pair of said sets of pins.

13. The system of claim 1 wherein said rod has a completely smooth outer surface.

14. The system of claim 1 including a second rod, each of said rods being carried by a portion of said coupling, and each of said portions of said coupling carrying a respective rod being provided with mating roughened surfaces so as to permit a virtually infinite number of gradations in the relative angulation of said rods.

15. In a method of treating a bone fracture by use of an external fixation system which includes mounting sets of pins from a frame on longitudinally opposite sides of the bone fracture with the frame including longitudinally extending rods secured to coupling means, the improvement being providing as at least one of the coupling means a sleeve member mounted around a respective rod with an inner stop mounted on the rod on the side of the sleeve member toward the bone fracture and with a remote stop mounted on the rod on the side of the sleeve remote from the bone fracture, forming the sleeve member from a housing having a longitudinal bore with an inner sleeve located in the bore and with the inner sleeve having an outer diameter less than the diameter of the housing bore to provide clearance therebetween whereby the inner sleeve may tilt within the housing, removably positioning a stabilizing insert in the clearance between the inner sleeve and the housing, slidably mounting the rod in the inner sleeve, mounting each stop against the sleeve member to minimize any sliding movement of the rod in the sleeve member during the initial stage of healing to maintain the bone fracture in static neutralization, and subsequently moving the inner stop a preselected distance away from the remote stop to permit a controlled amount of sliding movement of the rod in the sleeve member.

* * * * *